US006893405B2

(12) United States Patent
Kumar et al.

(10) Patent No.: US 6,893,405 B2
(45) Date of Patent: May 17, 2005

(54) ANALYSIS OF SLEEP APNEA

(75) Inventors: Anand Kumar, Amsterdam (NL);
Winni Hofman, Amsterdam (NL);
William Burzelewski, Danville, CA (US)

(73) Assignee: Medcare Flaga hf, Reykjavik (IS)

( * ) Notice: Subject to any disclaimer, the term of this patent is extended or adjusted under 35 U.S.C. 154(b) by 79 days.

(21) Appl. No.: 10/348,676

(22) Filed: Jan. 22, 2003

(65) Prior Publication Data

US 2003/0139691 A1 Jul. 24, 2003

Related U.S. Application Data

(60) Provisional application No. 60/350,770, filed on Jan. 22, 2002.

(51) Int. Cl.$^7$ ................................................. A61B 5/00
(52) U.S. Cl. ........................ 600/538; 600/534; 600/529
(58) Field of Search .................................. 600/529–538

(56) References Cited

U.S. PATENT DOCUMENTS

| 4,777,962 | A | * | 10/1988 | Watson et al. | ............... 600/529 |
| 4,815,473 | A | * | 3/1989 | Watson et al. | ............... 600/534 |
| 5,191,893 | A | * | 3/1993 | Reiten | ........................ 600/534 |
| 6,306,088 | B1 | * | 10/2001 | Krausman et al. | .......... 600/301 |

* cited by examiner

*Primary Examiner*—Robert L. Nasser
(74) *Attorney, Agent, or Firm*—Jaeckle Fleischmann & Mugel, LLP

(57) ABSTRACT

A non-intrusive and quantitative method and apparatus for diagnosing sleep apnea and detecting apnea events by monitoring during sleep abdominal effort and thoracic effort, determining the phase of each effort, determining the difference in phase between each type of effort, and then determining the rate of phase angle change and standard deviation over time. Also provided may be treatment when apnea events are detected to trigger therapy apparatus such as airway positive pressure apparatus.

14 Claims, 9 Drawing Sheets

SYNCHRONOUS

CHEST

ABDO

ASYNCHRONOUS

CHEST

ABDO

PARADOXICAL

CHEST

ABDO

SYNCHRONOUS

CHEST   0°   15°

ABDO

ASYNCHRONOUS

CHEST   50°

ABDO

PARADOXICAL

CHEST   180°   165°

ABDO

ANALYSIS OF SLEEP APNEA

This application claims the benefit of U.S. Provisional Application Ser. No. 60/350,770, filed Jan. 22, 2002.

BACKGROUND

Obstructive Sleep Apnea one of the most common disorders in the U.S. Lower oxygen levels associated with Obstructive Sleep Apnea (OSA) is now known to be a major cause of cardiovascular morbidity including heart attack and stroke. At present expensive polysomnography is used to identify these patients but not on a sufficient scale to provide diagnosis as a practical matter. The development of a diagnostic system which can allow simplified diagnosis of obstructive sleep apnea by the primary care physician would be a major step. The prevention of hundreds of thousands of annual excess deaths, stroke and heart attacks associated with obstructive sleep apnea through simplified recognition of this disorder is the most important purpose of the present invention. These excess deaths are occurring annually in a great part due to the lack of availability of this technology resulting in a vast pool of undiagnosed cases of Sleep Apnea and other breathing disorders. Despite the fact that obstructive sleep apnea is easily treated, both the patient and the family are often completely unaware of the presence of this dangerous disease, thinking the patient just a"heavy snorer".

Obstructive sleep apnea often develops insidiously as a patient enters middle age and begins to snore. The major cause is an increase in fat deposition (often age related) in the neck which results in narrowing of the airway. (In fact the probability that a 40 year old has sleep apnea is directly related to his or her neck circumference). When the muscle tone of the upper airway diminishes during sleep coupled with negative pressure associated with inspiration through this somewhat narrow airway results in collapse of the upper airway in a manner analogous to the collapse of a cellophane straw. This results in airway obstruction and, effectively chokes off all air movement The choking patient (still asleep) begins to struggle and inhales more forcibly, thereby, further lowering upper airway pressure and causing further collapse of the upper airway. During this time, substantially no air movement into the chest occurs and the patient experiences a progressive fall in oxygen (similar to the fall occurring early in drowning). The fall in oxygen produces central nervous system stimulation contributing to hypertension and potential heart and blood vessel injury and finally results in arousal. Upon arousal, increase in airway muscle tone opens the airway and the patient rapidly inhales and ventilates quickly to correct the low oxygen levels. Generally, the arousal is brief and the patient is not aware of the arousal (or of the choking since this occurs during sleep). Once oxygen levels have been restored, the patient begins again to sleep more deeply, upper airway tone again diminishes, the upper airway collapses and the cycle is repeated stressing the heart with low oxygen in a repetitive fashion. Often this repeating cycle over many years eventually results in damage to the heart muscle and/or the coronary arteries. As the patient ages, the consequences of undiagnosed obstructive sleep apnea is often either a progressive decline in heart muscle function (and eventual heart failure) or heart infarction.

The duration and severity of each apnea event is quite variable from patient to patient and with the same patient throughout the night. Indeed, the disease process represents a spectrum of severity from mild snoring, which is associated with incomplete and inconsequential airway obstruction, to severe apneas which can result in fatal hypoxemia.

This disease commonly results in excessive daytime sleepiness and can disrupt cognitive function during the day due to fragmentation of sleep during the night associated with recurrent arousals of which the patient is not aware.

Although this disease commonly affects obese patients, it may occur in patients with any body habitus. Because this disease is so common and because it presents with the subtle and common symptoms of excessive daytime sleepiness, morning headache, and decreasing ability to concentrate during the day, it is critical that an inexpensive technique for accurately diagnosing and treating this disease be developed. Traditionally, this disease has been diagnosed utilizing a complex and expensive multi-channel polysomnogram. This is generally performed in a sleep lab and involves the continuous and simultaneous measurement and recording of an encephalogram, electromyogram, electroculogram, chest wall plethysmogram, electrocardiogram, measurements of nasal and oral air flow, and pulse oximetry. These, and often other, channels are measured simultaneously throughout the night and these complex recordings are then analyzed to determine the presence or absence of sleep apnea.

The problem with this traditional approach is that such complex sleep testing is expensive and limited to laboratories. Since sleep apnea is so common, the cost of diagnosing obstructive sleep apnea in every patient having this disease in the United States is prohibitive. It is critical that a new, inexpensive technique of accurately diagnosing sleep apnea be developed.

For example, nocturnal oximetry alone has been used as a screening tool to screen patients with symptoms suggestive of sleep apnea to identify whether or not oxygen desaturations of hemoglobin occur. Microprocessors have been used to summarize nocturnal oximetry recordings and to calculate the percentage of time spent below certain values of oxygen saturation However, oxygen desaturation of hemoglobin can be caused by artifact, hypoventilation, ventilation perfusion mismatching. For these reasons, such desaturations identified on nocturnal oximetry are not specific for sleep apnea and the diagnosis of sleep apnea has generally required expensive formal polysomnography.

The diagnosis of sleep disorders often involves polysomnography (PSG), the monitoring and recording over an extended period of time of the temporal variations in the amplitude of the patient's sleep-impacted, physiological parameters, including: heart rate, eye blink activity, airflow rate, thorax and abdomen respiration rates, the blood's oxygen saturation level, electroencephalograms (EEG), electrooculograms (EOG), and electromyograms (EMG). Such intensive monitoring activities are typically conducted in clinical settings by trained PSG technicians who utilize expensive monitoring equipment having multiple sensors that are tethered to a centralized recording system and power supply.

For several decades, the recordings of such physiological parameters were provided by strip chart recorders that produced long strips of paper with ink markings that displayed the varying physiological parameters. The clinician would then examine such records and "score" each abnormal sleep event that occurred. This practice continues today with the clinician now viewing computer screens displaying the varying physiological parameters.

More recently, a number of portable recording systems for screening and diagnosing sleep disorders have been marketed. These systems range from multi-channel, PSG-style systems to much simpler units that monitor only one or more of the possible physiological parameters of interest.

However, these multi-channel, portable systems remain technically complex, expensive and usually require trained PSG technicians to supervise their use.

Some of the newer of these portable systems offer comprehensive software for display and analysis of the collected sleep data, and some offer automatic sleep event scoring. However, such scoring has been found to have varying degrees of reliability due to the technical problems associated with assuring good signal fidelity in the monitored parameters. Thus, all of these systems recommend for accurate identification of abnormal sleep events that the data be interpreted and evaluated by experienced clinicians or trained PSG technicians.

Since PSG scoring is largely subjective, experienced scorers can generally interpret with good accuracy the action and interactions of poorly shaped and time skewed signals. Although these distortions are commonly accepted as normal for manual scoring, such poor fidelity signals would be unsatisfactory for automated or computer-based scoring.

All of the current, portable sleep testing systems share common, less-than-desirable features for home use: (1) they are bedside portable, but their size and weight does not allow the patient to be ambulatory, which can be essential for diagnosing patients problems such as excessive sleepiness, (2) they are not designed for unattended use-a technician must come to the home for set-up, disconnection and data retrieval, (3) patients must be outfitted with an array of tethered electrode wires and sensors for connection to bulky body monitors or table-top consoles, and (4) most require subjective analysis of the data by highly trained, sleep professionals.

Recognizing the need for an improved apparatus or method for diagnosing of the various medical conditions of a fully ambulatory subject who exhibits temporal variations in various physiological parameters as a result of this medical condition, it is therefore a general object of the present invention to provide a novel method and ambulatory, distributed recorders system to meet such needs.

SUMMARY OF THE INVENTION

The present invention relates to a method of diagnosing sleep apnea that non-intrusive and quantitative. Diagnosis of sleep apnea can be achieved by monitoring the phase angle between abdominal effort during sleep and thoracic effort during sleep, determining the phase of each effort, determining the difference in phase between each type of effort, and then determining the rate of phase angle change over time. The instability of the phase angle correlates with respiratory distress index (RDI) and thus is a useful tool for diagnosis.

The invention also provides for treatment to detect events and trigger therapy apparatus such as airway positive pressure apparatus whether operating in CPAP, multi-level CPAP, IPAP or EPAP modes.

The therapy is a pressurized air infusion device and the system further determines the rate of change of phase angle between abdominal effort in breathing and thoracic effort in breathing for determining optimal pressure of the infusion device with or without other signals of polysomnograpy.

DETAILED DESCRIPTION OF THE INVENTION

In particular, the invention recognizes that the phase angle, the difference between the phase of abdominal effort during breathing and thoracic effort during breathing, while useful in diagnosis or screening is not the most useful factor, but rather the change in phase angle as a function of time is. For instance, thoracic and abdominal effort could be measured by mechanical means and graphed on a strip chart as a function of time, the phase of each type of effort could be determined as well as the change of phase, and the instability of the phase angle could be determined. The degree of uncertainty then is used to measure the degree of breathing disturbance the patient demonstrates.

Figure 1:
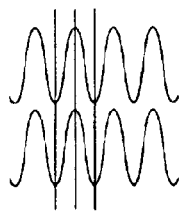
FIG. 1 is a symbolic representation of abdominal and thoracic effort during breathing and the phase angle between each type of effort and shows how when breathing is "synchronous", "asynchronous" and "paradoxical".
Figure 1:
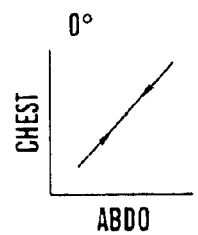
Figure 1:
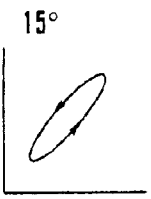
Figure 1:
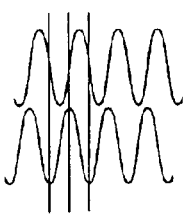
Figure 1:
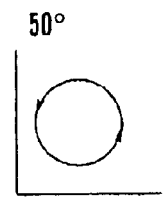
Figure 1:
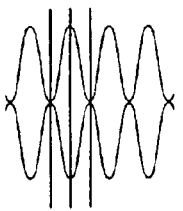
Figure 1:
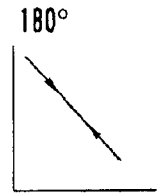
Figure 1:
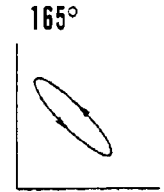
Figure 2:
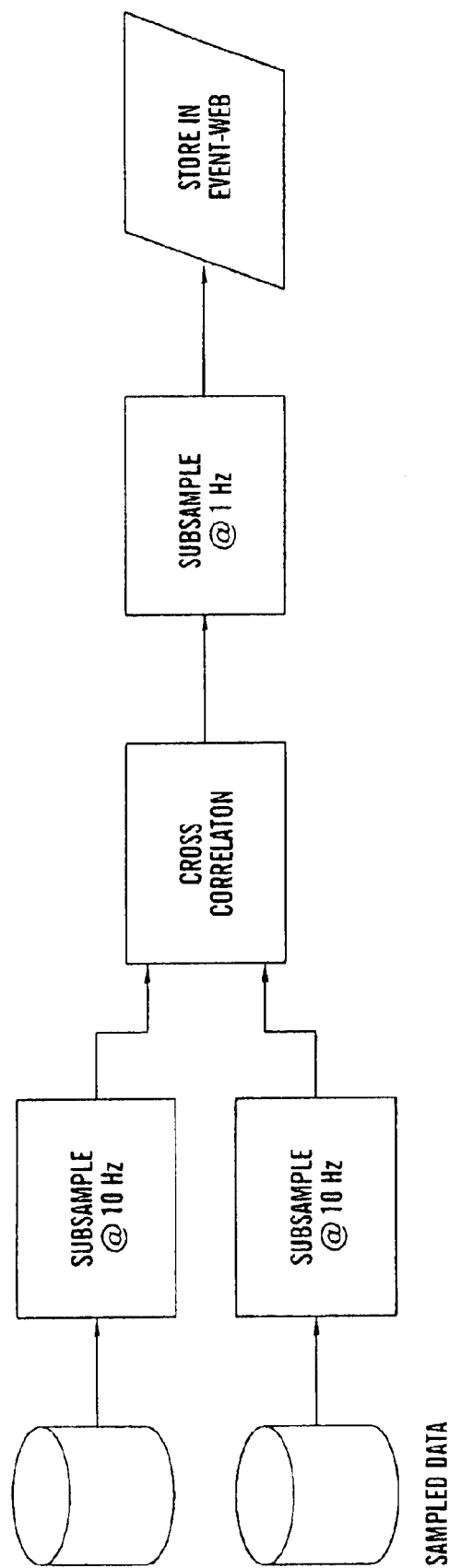
FIG. 2 depicts the general process of monitoring and calculating the change of phase angle.
Figure 3:
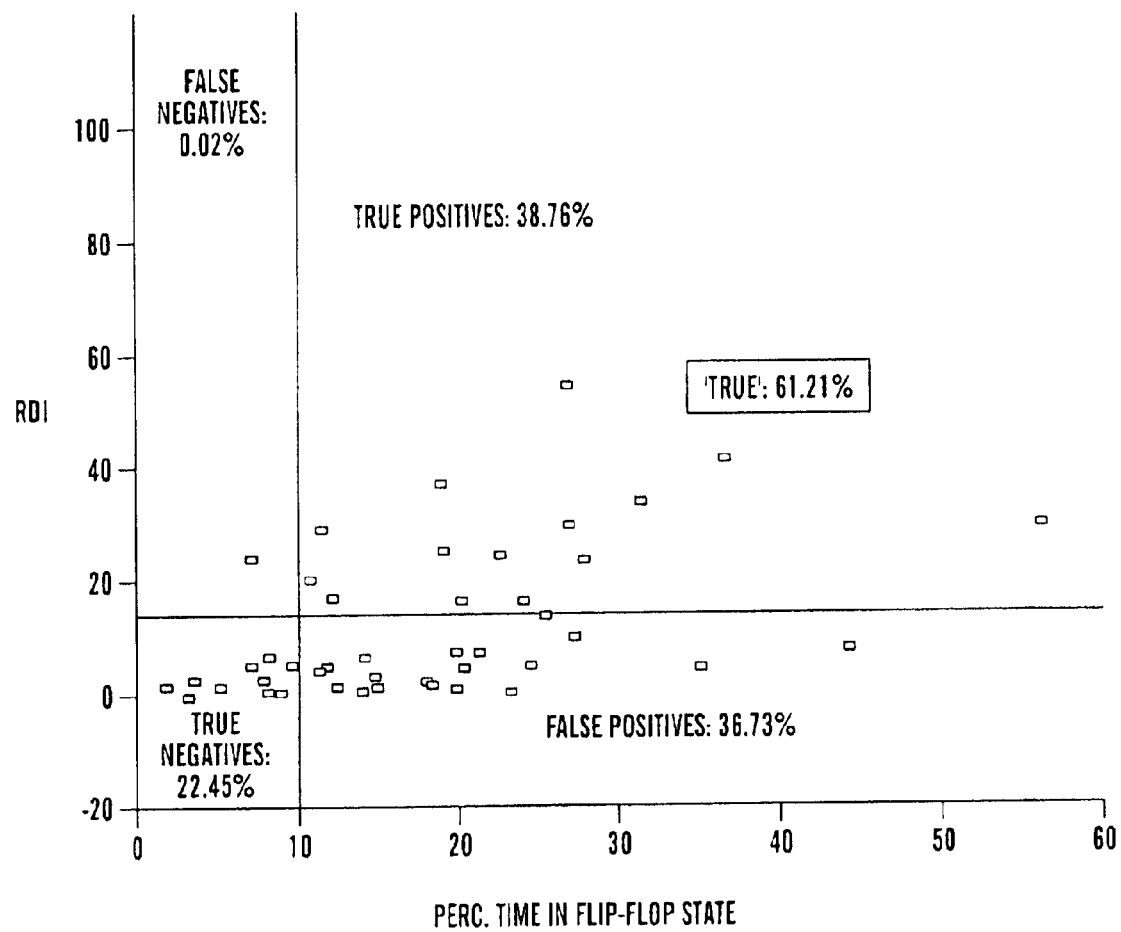
FIG. 3 shows the data correlation of 49 patients graphing the percentage of time in instable phase angle versus the respiratory distress index of each patient.
Figure 4:
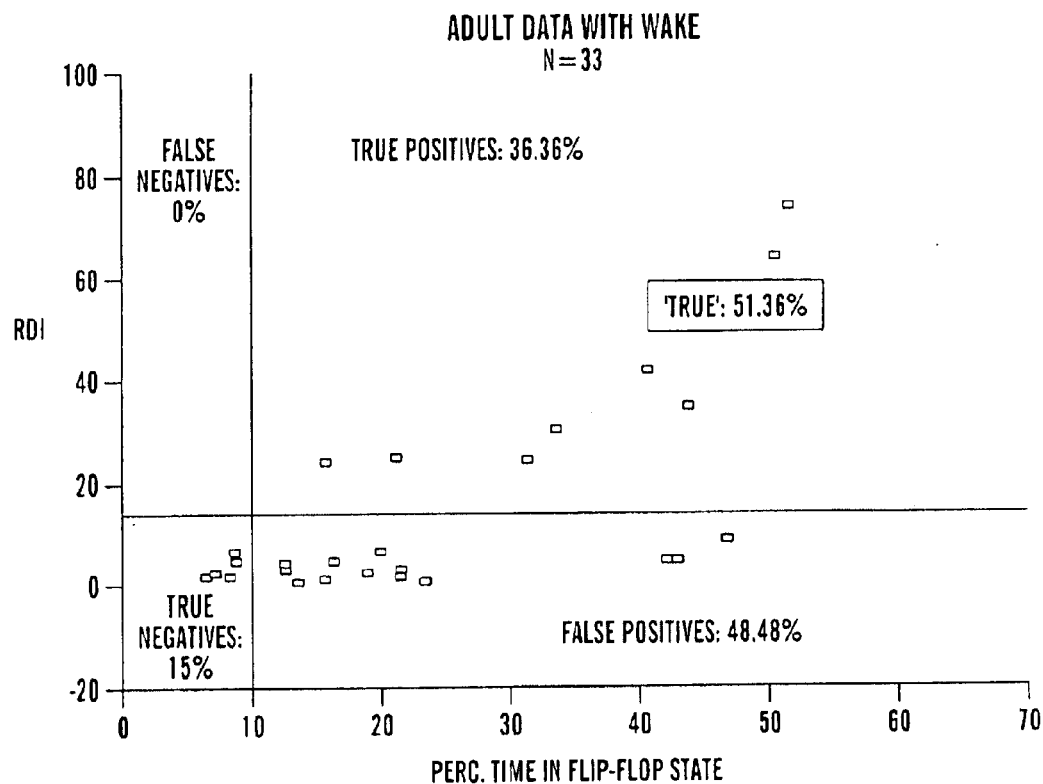
FIG. 4 shows the data correlation of a study 21 children graphing the percentage of time in instable phase angle versus the respiratory distress index of the patient.
Figure 5:
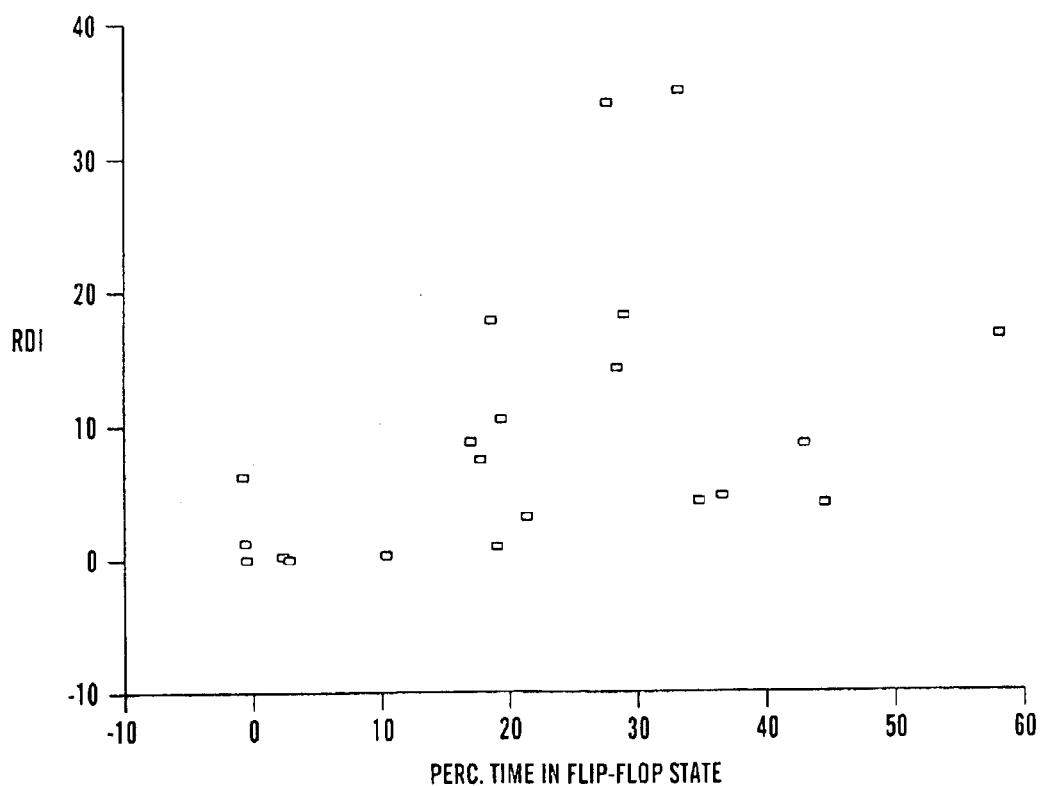
FIG. 5 shows the data correlation of 33 asleep patients graphing the percentage of time in instable phase angle versus the respiratory distress index of each patient.
Figure 6:
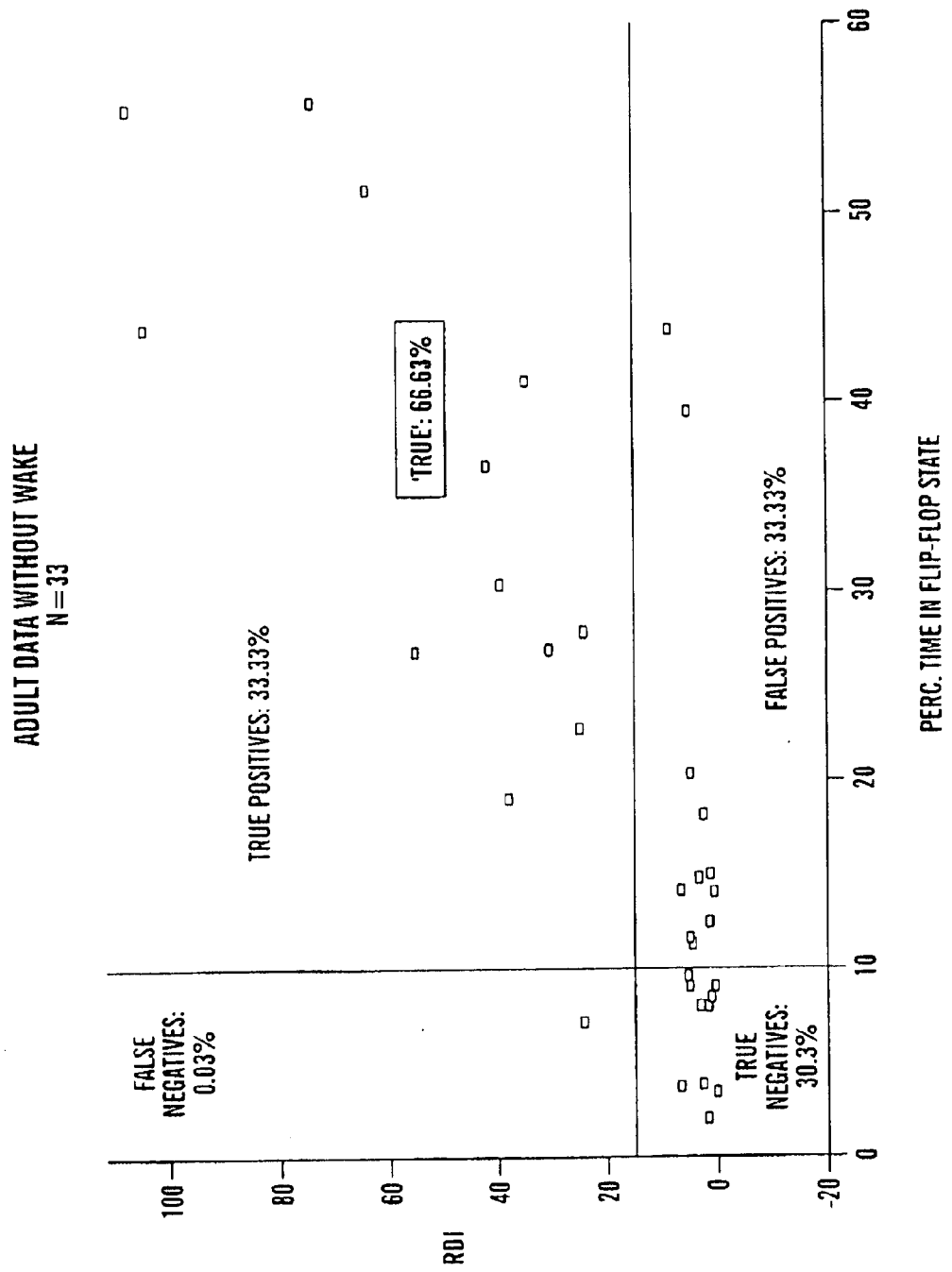
FIG. 6 shows the data correlation of the same 33 asleep patients (where as periods with wake stages are removed) graphing the percentage of time in instable phase angle versus the respiratory distress index of each patient.
Figure 7:
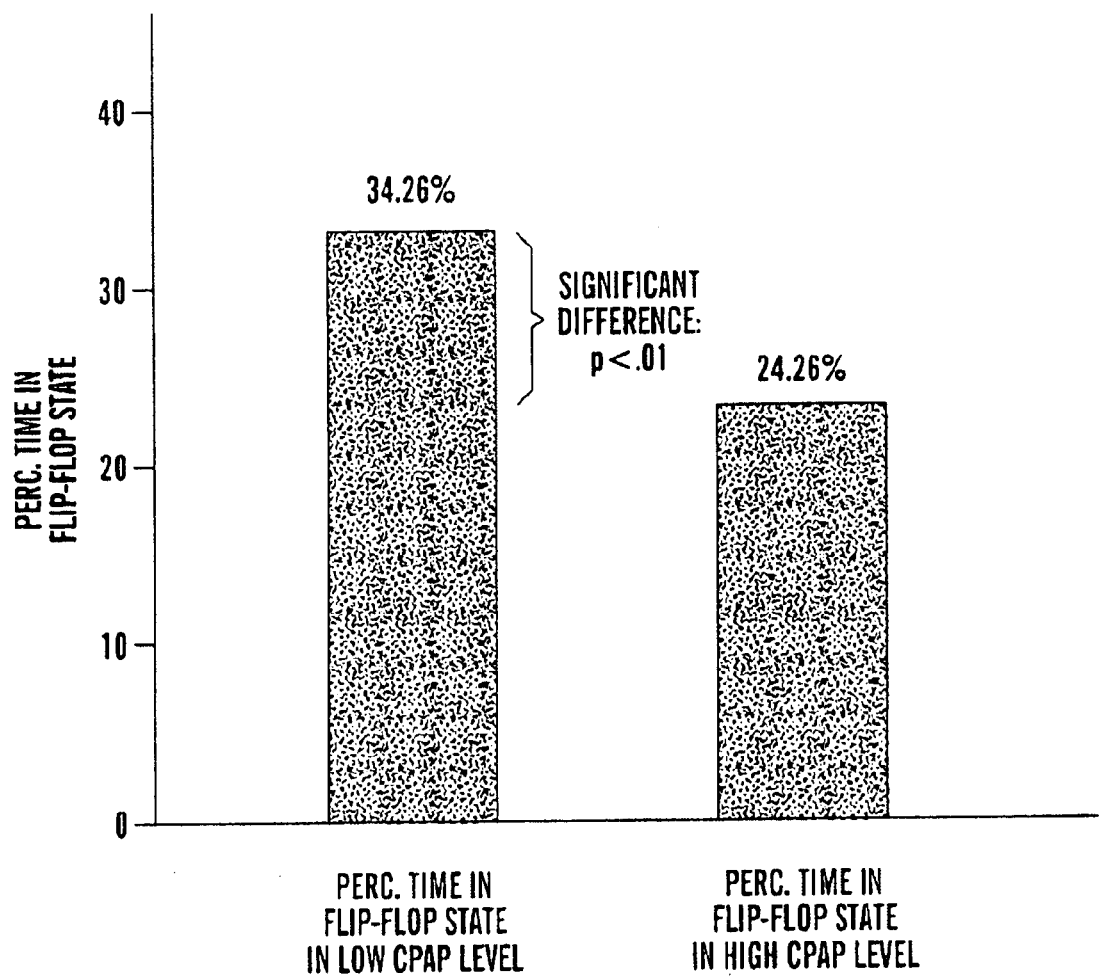
FIG. 7 shows the phase angle change data generated by a patient displayed in graphic form showing standard deviations from the norm.
Figure 8:
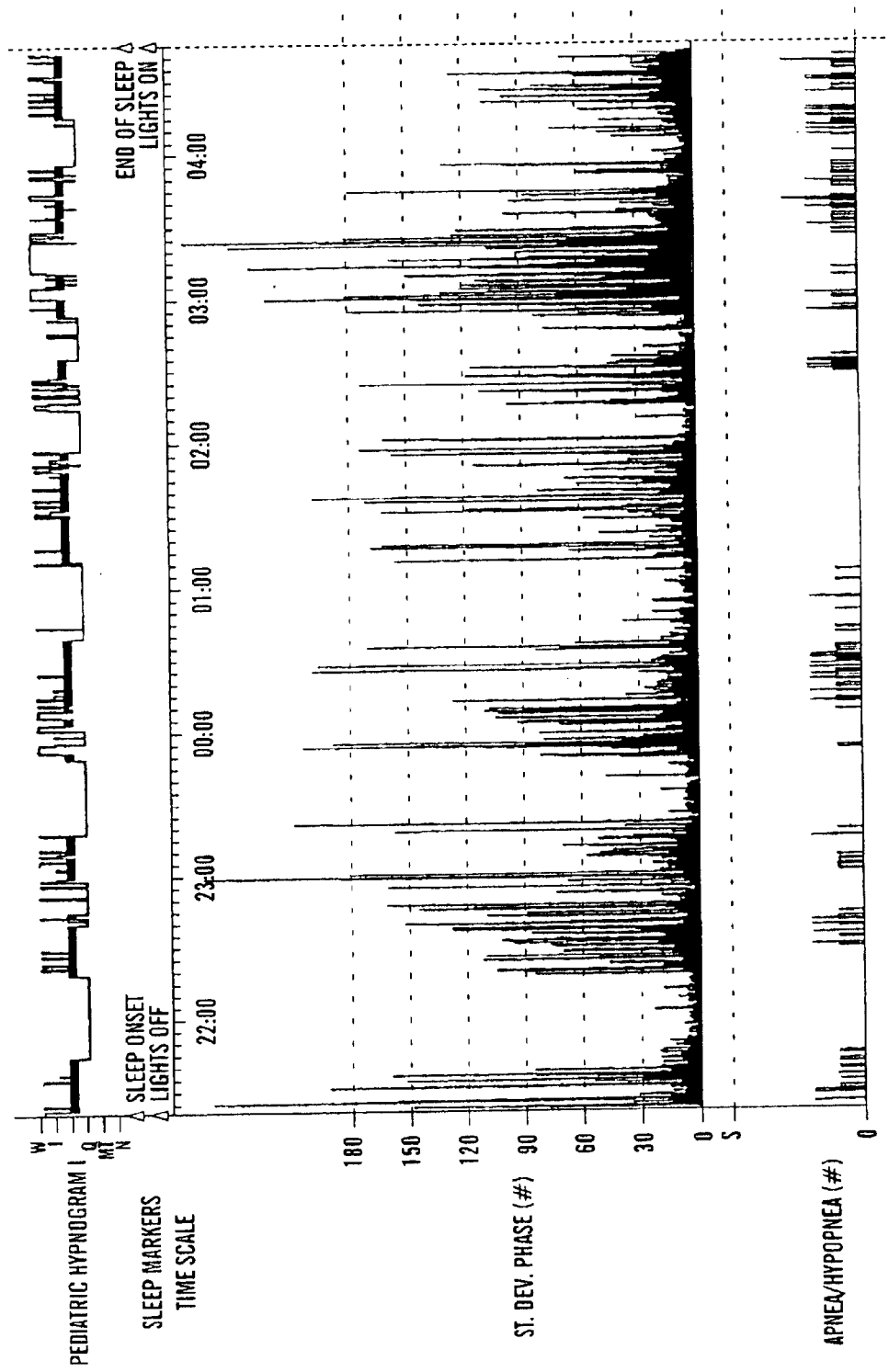
FIG. 8 shows data phase angle change data in graphic form.
Figure 9:
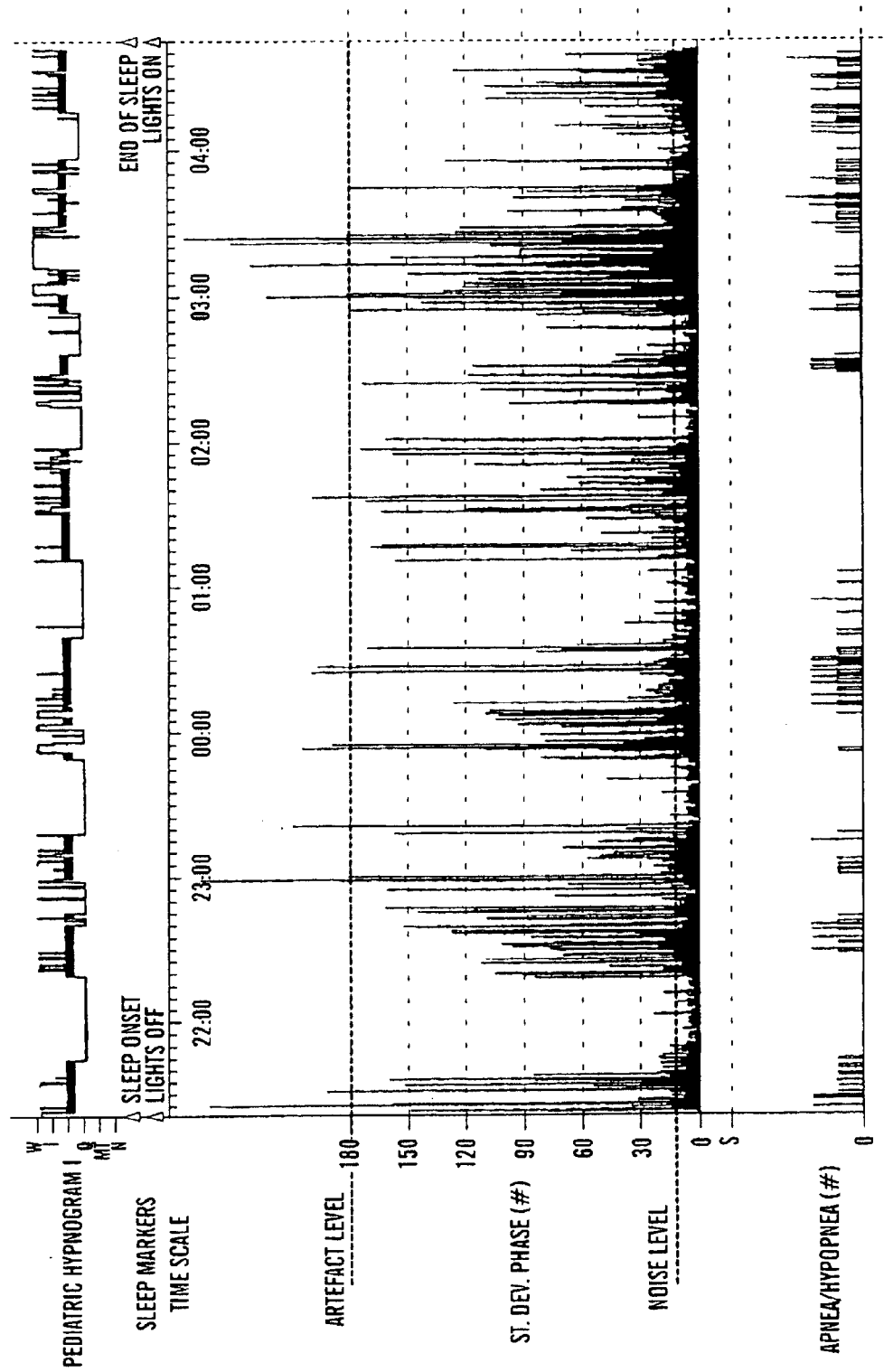
FIG. 9 shows data phase angle change data in graphic form.
Figure 10:
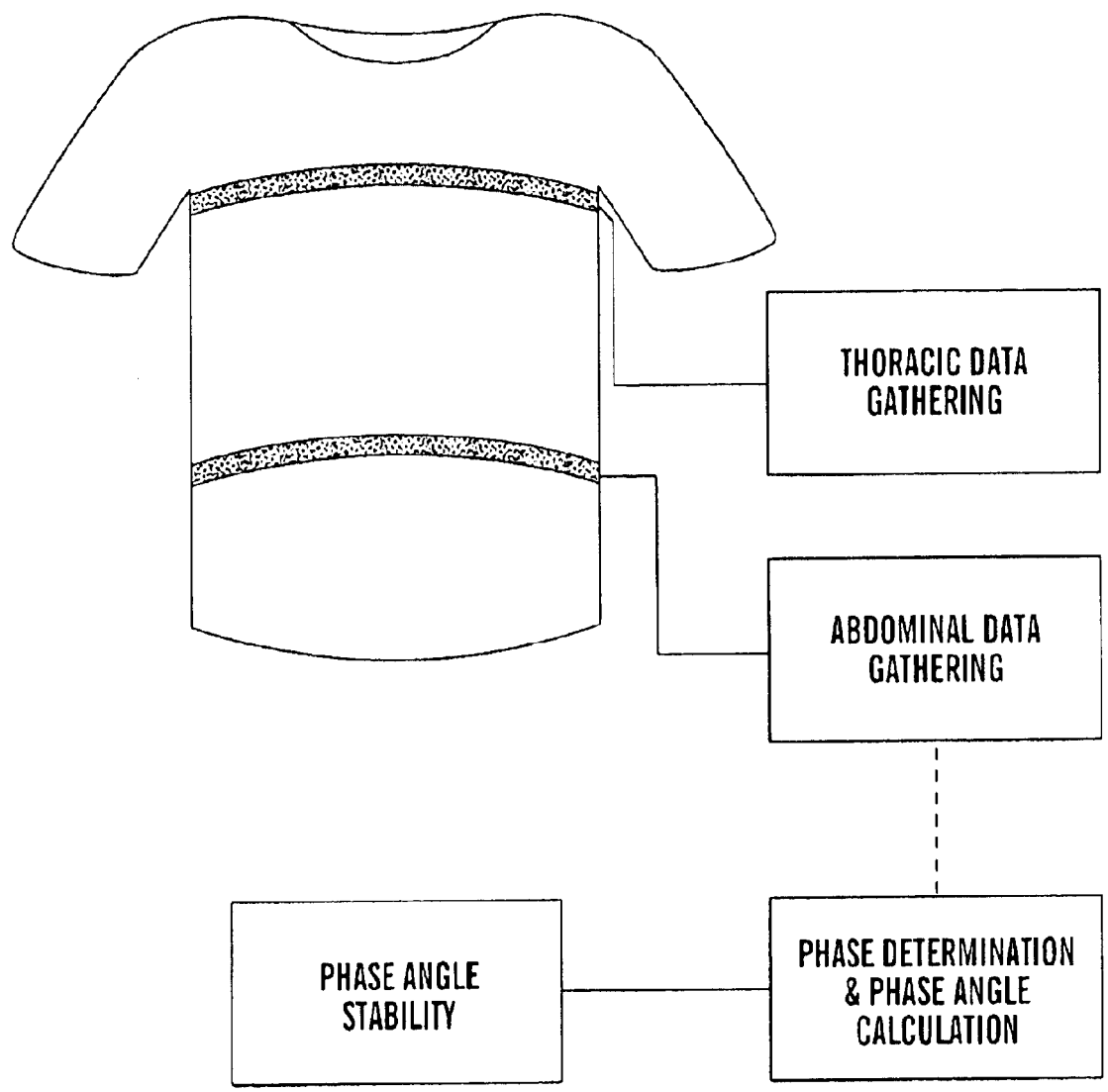
FIG. 10 illustrates a disposable, wearable garment for diagnosing a patient.

According to FIG. 2 the signals are first digitized and data is stored in a computer fife. The calculations have no restriction on sample rate. It is however expected that sample rate satisfies the Nyquist rule. For respiration, 10 Hz sample rate is nominal value. The computer file reads the signals and performs phase calculation off-line. The method for phase calculation is by cross-correlation between two signals. The distance between two adjacent maxima in the cross correlation curve estimates the dominant period time. The distance between zero lag and the nearest maximum is a measure of phase lag. This value is in seconds. Phase in degrees is estimated by the division of estimated phase lag by estimated period time.

In another method to reduce computational burden the user is given the option to sub-sample data at about 10 Hz. This ensures that recordings that have recorded respiratory signals at high sample rates will not result in unacceptable long phase calculation times. The results of the phase calculation are stored at 1-second intervals (to reduce the storage requirements). The result is a value per second between $-180°$ and $+180°$ which is indicative for the current phase angle between the two effort signals. The values can be plotted per second in a signal window or as a mean value over a longer period (30 seconds) in an overview window.

Method of Determining Change in Phase Angle

In a means for analyzing data the standard deviation of the phase angle between the two respiratory signals is calculated over a sample period (generally 30 seconds but this period can be adjusted). In a window that gives an overview for a prolonged sample period (perhaps a night's sleep), the standard deviation of the phase angle as well as the original phase values are plotted as a function of time. This gives instantaneous information about the variability of the phase angle over sample period. The changes in phases can also be plotted by calculating differences between adjacent phase values.

Method to Calculate the Variability of Phase

The variability of the phase angle over a certain period is an indication of the extent to which the phase angle between the two effort signals fluctuates. The standard deviation of the phase angle over a certain period is a statistical method to calculate this variability. In one embodiment the standard deviation is presented for every 30 minutes. For diagnostic purposes, shorter period (10 seconds) is chosen to calculate the standard deviation of the phase angle. The following steps are used to calculate this index:

1. All phase angle values are made absolute values, so that all negative values are made positive (it does not matter if the phase angle is positive or negative);
2. Phase angle values higher than 180° are removed to correct for evident artifacts; and
3. The standard deviation for each 10 second duration is calculated.

Other methods for calculating variability of phase angle can be employed. However, the method must be chosen so that variability can be measured. The measure of variability in one case was chosen so that for the whole the night the number of 10 sec periods with more than 10 standard deviation was summed. This measure was termed a flip-flop state and the percentage of time is calculated. It is called the Flip Flop State Index. The Flip Flop State Index is directly related to upper airway obstruction.

Method to Validate and Generate Normative Data

Polysomnography (PSG) data from various sleep laboratories was used. Registered polysomnography technicians or clinicians manually scored this data for apnea's, desaturations and sleep stages. Data is from patients who are diagnosed for sleep apnea. For each night, RDI (based on standard rules) was calculated for each patient. For each night, also the Flip Flop State Index was calculated as shown in FIGS. 3, 4, 5, 6, 8 and 9.

A highly significant correlation was found between the Flip Flop State Index and the respiratory disturbance index in a group of adults, indicating that the Flip Flop State Index was related to a high respiratory disturbance. If the Flip Flop State Index was higher than 0.1, then it was predicted that patient was an OSA patient. This prediction was validated against RDI numbers calculated independently. From these calculations. ROC and percentages of hits and misses were calculated.

Method to Use Flip-Flop State to Evaluate and/or Initiate CPAP Titration

In another group of apnea patients receiving CPAP treatment a lower phase variability was found in the part of the night with a high CPAP value than in the part of the night with a low CPAP value. Normative values of the Flip-Flop State Index calculated from this data should provide a tool to help judge whether the pressure too high or too low.

While thoracic abdominal asynchrony (TAA) is a known measure that has been used for COPD, other respiratory abnormalities and in paradoxical breathing during sleep, it has not been used in diagnosis of apnea. The study of paradoxical breathing, where the phase angle between abdominal effort and thoracic effort is about 90 degrees, has shown that long periods of paradoxical breathing are deleterious. However, no connection has been made between paradoxical breathing and apnea. Literature in this field has been more concerned with the absolute measure of phase angle rather than the rate of phase angle change with time.

The rate of change of phase angle correlates to the respiratory disturbance index (the number of times arousal from sleep occurs per hour). A correlation exists between the rate of change of phase angle and RDI, and thus apnea and hypopnea can be diagnosed.

In practice a patient is provided with a means for measuring thoracic and abdominal effort. Such equipment might include piezo belts, PDF belts, inductance or impedance measurement devices and the like. The design and function of the effort sensors is to allow for monitoring the volume in each region as a function of time and allow determination of the phase of abdominal effort and thoracic effort so that they can be compared and the phase angle difference between the two can be determined. The difference in the phases of the two types of efforts changes over time and is stored for evaluation.

Besides a manual approach to determining phase angle instability, automated means can be used as well. For instance the abdominal and thoracic phase information could be collected and input into a computer with a software utility that calculates phase change and determines whether there is a significantly significant change or changes in a set of date. Likewise, this calculation could also be performed by a device with embedded-software on a chip, or analog hardware, or combination thereof.

What is claimed is:

1. A method for diagnosing sleep apnea comprising the steps of measuring thoracic volume of a patient as a function of time and determining the phase of the change of thoracic volume of said patient, measuring abdominal volume of said patient as a function of time and determining the phase of the change of abdominal volume of said patient, calculating the phase angle between said thoracic volume phase and said abdominal volume phase as a function of time, and observing changes of the phase angle over a selected time period to indicate the extent to which the phase angle between the two effort signals fluctuates.

2. The method according to claim 1 in which the phase angle calculation is made by cross-correlation between two signals created by the measurements, and the distance between two adjacent maxima in the cross correlation estimates the dominant period time with the distance between zero lag and the nearest maximum being a measure of phase lag with phase in degrees estimated by dividing estimated phase lag by the estimated period time.

3. The method according to claim 2 and further calculating the standard deviation of the phase angle over a certain time period to use as a statistical method to for the diagnosis.

4. The method according to claim 2 in which data from the measurements are sub-sampled at predetermined intervals of about 10 Hz, and the results of the phase calculation stored at about 1-second intervals.

5. The method according to claim 1 in which the measurements and calculations are analyzed to determine the standard deviation of the phase angle between the two effort signals over a sample period.

6. The method according to claim 5 in which the variability is measured over substantially the whole sleep period in about 10 second periods with more than about 10 standard deviations summed to calculate a flip-flop state index directly related to upper airway obstruction.

7. The method according to claim 6 in which a flip-flop state index higher than about 0.1 is used as a predictor of obstructive sleep apnea.

8. The method according to claim 1 in which a respiratory distress index by the number of times of arousal from sleep in a predetermined time is correlated with the instability of the phase angles for the diagnosis of apnea and/or hypopnea.

9. The method according to claim 1 in which the abdominal and thoracic phase information is input into a computer with a software utility that calculates phase change and determines significant change or changes in sets of data.

10. Apparatus for diagnosing sleep apnea comprising means for measuring thoracic effort and abdominal effort of a patient as a function of time and determining the phase of the change of each of the efforts, means for calculating the phase angle between the efforts as a function of time, means for plotting the measurements, determinations and calculations, and observing changes of the phase angle over a selected time period to indicate the extent to which the phase angle between the two effort signals fluctuates, means for determining change in phase angle, and statistical means for determining the standard deviation of the phase angle.

11. Apparatus according to claim 10 and further comprising means for recording the phase angles and standard deviations over time during sleep.

12. Apparatus according to claim 11 and further comprising means for administering therapy when the standard deviation exceeds a predetermined value.

13. Apparatus according to claim 12 in which the therapy comprises a pressurized air infusion device and further comprising means for determining the rate of change of phase angle between abdominal effort in breathing and thoracic effort in breathing and using the determining means with or without other signals of polysomnography for determining optimal pressure of the infusion device.

14. Apparatus according to claim 10 and further comprising means for determining the rate of change of phase angle between abdominal effort in breathing and thoracic effort in breathing.

* * * * *